(12) United States Patent
Sangita et al.

(10) Patent No.: US 7,582,653 B2
(45) Date of Patent: Sep. 1, 2009

(54) MERCAPTOPHENYL NAPHTHYL METHANE COMPOUNDS AND SYNTHESIS THEREOF

(75) Inventors: Sangita, Lucknow (IN); Atul Kumar, Lucknow (IN); Man Mohan Singh, Lucknow (IN); Girish Kumar Jain, Lucknow (IN); Puvvada Sri Ramanchandra Murthy, Lucknow (IN); Suprabhat Ray, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 11/812,251

(22) Filed: Jun. 15, 2007

(65) Prior Publication Data

US 2007/0244161 A1    Oct. 18, 2007

Related U.S. Application Data

(62) Division of application No. 10/809,845, filed on Mar. 26, 2004, now Pat. No. 7,250,446.

(60) Provisional application No. 60/458,401, filed on Mar. 31, 2003.

(51) Int. Cl.
| | |
|---|---|
| A61K 31/4453 | (2006.01) |
| A61K 31/40 | (2006.01) |
| A61K 31/135 | (2006.01) |
| A61K 31/12 | (2006.01) |
| C07D 295/04 | (2006.01) |
| C07C 317/14 | (2006.01) |
| C07C 321/00 | (2006.01) |

(52) U.S. Cl. .......... 514/319; 514/428; 514/648; 514/682; 546/205; 548/576; 564/315; 568/31; 568/42

(58) Field of Classification Search ........ 514/601, 514/333, 422, 438, 675, 428, 319, 648, 682; 546/212, 205; 548/527, 576; 549/29; 564/102, 564/315; 568/28, 31, 42
See application file for complete search history.

(56) References Cited

U.S. PATENT DOCUMENTS

| 5,807,873 | A | * | 9/1998 | Nicolai et al. ............... 514/336 |
| 5,962,531 | A | | 10/1999 | Rotstein et al. |
| 6,150,397 | A | | 11/2000 | Rotstein et al. |

OTHER PUBLICATIONS

Yang et al., Triplet state and photolysis of S-phenyl 1-thionaphthoate, 1996, Journal of Photochemistry and Photobiology A: Chemistry 99, p. 49.*

* cited by examiner

*Primary Examiner*—Kamal A Saeed
*Assistant Examiner*—Kristin Bianchi
(74) *Attorney, Agent, or Firm*—Buchanan, Ingersoll & Rooney P.C.

(57) ABSTRACT

Novel mercaptophenyl naphthyl methane compounds, their pharmaceutically acceptable salts and compositions comprised thereof are useful for the prevention or treatment of various medical indications associated with estrogen dependent diseases or syndromes related to osteoporosis, bone loss, bone formation, cardiovascular disorders, neurodegenerative disorders, menopausal disorders, physiological disorders, diabetes disorders, prostatic carcinoma, cancer of breast, cancer of uterus, cancer of the cervix and cancer of the colon, threatened or habitual abortion, obesity, ovarian development or function, post-partum lactation and depression.

15 Claims, 1 Drawing Sheet

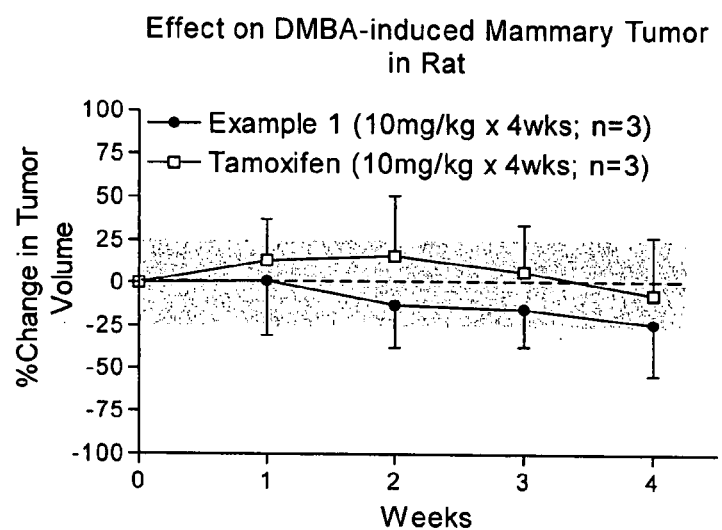
Figure 1. Evaluation of anti-cancer activity by *in vivo* effect of DMBA-induced mammary Tumor in Rat

MERCAPTOPHENYL NAPHTHYL METHANE COMPOUNDS AND SYNTHESIS THEREOF

CROSS-REFERENCE TO EARLIER APPLICATIONS

This application is a divisional of U.S. patent application Ser. No. 10/809,845, filed Mar. 26, 2004, now allowed, which claims benefit under 35 U.S.C. § 119 of U.S. Provisional Application No. 60/458,401, filed Mar. 31, 2003, both hereby expressly incorporated by reference and assigned to the assignee hereof.

BACKGROUND OF THE INVENTION

1. Technical Field of the Invention

The present invention relates to the field of pharmaceuticals and organic chemistry and provides new substituted mercaptophenyl naphthyl methane derivatives, their pharmaceutically acceptable salts and compositions that are useful for the prevention or treatment of various medical indications associated with estrogen dependent diseases or syndromes, preferably in prevention or treatment of diseases and syndromes caused by:

(a) estrogen deficient or deprivation state in a mammal, in particular osteoporosis, bone loss, bone formation, cardiovascular effects more particularly hyperlipidaemia, thrombosis and vasomotor system, neurodegenerative effects such as stroke, senile dementia-Alzheimer type and Parkinson disease, menopausal symptoms including hot flushes, urogenital atrophy, depression, mania, schizophrenia and the like, urinary incontinence, relief of dysmenorrhea; relief of dysfunctional uterine bleeding, an aid in ovarian development, treatment of acne and hirsutism;

(b) estrogen dependent or estrogen independent cancers such as prostatic carcinoma, cancer of breast, cancer of uterus, cancer of the cervix and cancer of the colon;

(c) an aid in ovarian development or function;

(d) control or regulation of fertility in humans and in other animals;

(e) prevention of threatened or habitual abortion;

(f) suppression of post-partum lactation;

(g) physiological disorders such as obesity, depression etc.;

(h) regulation of glucose metabolism in non-insulin dependent diabetes mellitus.

The present invention further relates to the processes for the preparation of pharmaceutically active compounds, their pharmaceutically acceptable salts and compositions of the principal aspect of the present invention.

2. Description of Background and/or Related and/or Prior Art

Menopause, the transition in women from the reproductive to the non-reproductive stage of life, is characterized by the cessation of menstruation and occurs at an average age of fifty years. The post-menopausal state is characterized by changes in the levels of circulating sex hormones, the most dramatic of which is the reduction in plasma levels of 17-beta-estradiol to less than ten percent of pre-menopausal values. Clinical and epidemiological studies have shown that the post-menopausal state is an important risk factor for a number of chronic disorders and is often referred to as Post Menopausal Syndrome. In view of the fact that the current life span of women is about eighty years, women spend approximately one-third of their lives in the post-menopausal state. This means that the potential for chronic effects of the post-menopausal state on women's health is greater today than at the turn of the century when life expectancy was considerably shorter.

Estrogen deficiency is the most important risk factor associated with Post Menopausal Syndrome. Some of the major effects of the Post Menopausal Syndrome that are source of greatest long-term medical concern include osteoporosis, bone loss, bone formation, cardiovascular effects more particularly hyperlipidaemia, thrombosis and vasomotor disorders, neurodegenerative effects such as stroke, senile dementia-Alzheimer type and Parkinson disease, menopausal symptoms including hot flushes, urogenital atrophy, depression, mania, schizophrenia, urinary incontinence, relief of dysmenorrhea; relief of dysfunctional uterine bleeding, an aid in ovarian development, treatment of acne, hirsutism.

Osteoporosis can be defined as a reduction in bone mass per unit volume with an alteration in bone microarchitecture that results in an increased susceptibility to fractures. It is not surprising that the most common fractures are those associated with bones, which are highly dependent on trabecular support, for example the vertebrae, the neck, and the weight bearing bone such as the femur, and the fore arm. Indeed the hip fracture, collies fractures and vertebrae crush fractures are hallmarks of post-menopausal osteoporosis. In most cases, bone loss occurs as a result of increased bone destruction (resorption) relative to bone formation and most women lose from about 20% to 60% of the bone mass in the trabecular compartment of the bone within 3 to 6 years after the menopause. Osteoporosis, more particularly the post-menopausal osteoporosis represents a major problem in women health care and poses a risk to quality of life during old age. Efforts to reduce this risk factor and incidence of fractures have resulted in the development of compounds that conserve skeletal mass by inhibiting bone resorption and/or by enhancing bone formation (Dwivedi I, Ray S, 1995 "Recent developments in the chemotherapy of osteoporosis" Progress in Drug Research 45, 289-338, Editor E Jucker, Birkhauser Vela; Marshall D H, Horsmann A, Nordin BEC, 1977, "The prevention and management of post-menopausal osteoporosis" Acta Obstet Gynecol Scand (Suppl) 65:49-56; Hutchinson T A, Polansky S M, Feinstein A R, 1979, "Postmenopausal estrogen protect against fractures of hip and distal radius: A care-control study" Lancet 2:705-709. Estrogen replacement therapy also has positive effect on CVS & CNS related disorders (Lobo RA, 1990, "Cardiovascular implication of estrogen replacement therapy" Obstetrics & Gynecology 84:185-245; Mendelson M E, Karas R H, 1994, "Estrogen and the blood vessel wall" Current opinion in Cardiology 1994:619-626; Stampfer M J, Colditz G A, 1991, "Estrogen replacement therapy and coronary heart disease: a quantitative assessment of the epidemiological evidence" Preventive Medicine 20:47-63).

Cardiovascular disease is another leading cause of morbidity and mortality in older women. Menopause and aging increase risk of atherosclerosis and coronary artery disease. An altered lipid profile is thought to be associated with this increased risk. Compared to men, pre-menopausal women are relatively more protected from cardiovascular diseases. This protection is gradually lost following menopause. This loss of protection has been linked to the loss of estrogen and in particular to the loss of estrogen's stationary phase ability to regulate the level of serum lipids. The nature of estrogens ability to reduce serum lipids is not well understood, but evidences indicate that estrogen can up-regulate LDL receptors in the liver which act to remove excess cholesterol. Additionally, estrogen appears to have some effects on the biosynthesis of cholesterol and other beneficial effects on cardiovascular health. Estrogen is also believed to directly influence vessel wall compliance, reduce peripheral resistance and prevent atherosclerosis. It is also reported that serum lipids in post-menopausal women having estrogen replacement therapy (ERT) return to concentrations found in the pre-menopausal state (Gruber C J, Tschugguel W, Schneeberger C, Huber J C, 2002, "Production and actions of estrogens" The New England Journal of Medicine 346:340-352; Bellino F L, Wise P M, 2003 "Nonhuman primate models of menopause workshop" Biology of Reproduction 68:10-18; Lobo R A 1990, "Cardiovascular implication of estrogen replacement therapy", Obstetrics and Gynecology 84:18S-24S; Medelson M E, Karas R D 1994, "Estrogen and the blood vessel wall", Current opinion in Cardiology, 1994 (9): 619-626). Based on available epidemiological data, the overall impact of these physiological and pharmacological actions of estrogen is an age independent reduction in cardiovascular mortality and morbidity in women (Knnel W H, Hjortland M, McNamara P M, 1976 "Menopause and risk of cardiovascular disease: The Framingham Study", Ann Int Med 8:5447-5552). Furthermore, a more recent analysis has concluded that post-menopausal estrogen replacement therapy reduces the risk of cardiovascular disease by approximately 50 percent (Stampfer M J, Colditz G A, 1991, "Estrogen replacement therapy and coronary heart disease: a quantitative assessment of the epidemiological evidence", Preventive Medicine 20:47-63).

There is growing interest in recent years on neuroprotective effects of estrogens for neurodegenerative conditions such as stroke, Alzheimer disease and Parkinson disease. Reports of greater brain damage in males than in females and in ovariectomized than intact female animals in ischemic stroke models are available. Estrogen is also known to increase density of N-methyl-D-aspartate receptors and increase neuronal sensitivity to input mediated by these receptors in neurons of hippocampus, the area involved in memory. The estradiol-depleted state in post-menopausal women has been correlated with increased incidence of stroke, cognitive defects, hot flashes, mood changes, and early onset and severity of Alzheimer disease. Some epidemiological data suggests that in post-menopausal women, estrogen deficiency is associated with decline in cognitive function and increased risk of Alzheimer's disease (Gruber C J, Tschugguel W, Schneeberger C, Huber J C, 2002 "Production and actions of estrogens", The New England Journal of Medicine 346:340-352; Dhandapani K M, Brann D W, 2002, "Protective effects of estrogen and Selective Estrogen Receptor Modulators in the brain" Biology of Reproduction 67:1379-1385). Short-term studies in human subjects have shown that increased levels of estrogen are associated with higher memory scores in post-menopausal women (Kampen D L, Sherwin B B, 1994 "Estrogen use and verbal memory in healthy postmenopausal women", Obstetrics & Gynecology 83:979-983; Ohkura T, Isse K, Akazawa K, Hamanioto M, Yoshimasa Y, Hagino N, 1995, "Long-term estrogen replacement therapy in female patients with dementia of the Alzheimer Type: 7 Case reports", Dementia 6:99-107). Furthermore, the administration of exogenous estrogen to surgically post-menopausal women specially enhances short-term memory. Moreover, the effects as epidemiological findings indicate that estrogen treatment significantly decreases the risk of senile dementia-Alzheimer type in women (Paganini-Hill A, Henderson V W, 1994, "Estrogen deficiency and risk of Alzheimer's disease in women", Am J Epidemiol 100:256-261; Ohkura T, Isse K, Akazawa K, Hamamoto M, Yoshimasa Y, Hagino N, 1995, "Long-term estrogen replacement therapy in female patients with dementia of the Alzheimer Type: 7 case reports", Dementia 6:99-107). While the mechanism whereby estrogens enhance cognitive function is unknown, it is possible to speculate that the direct effects of estrogen on cerebral blood flow (Goldman H, Skelley Eb, Sandman C A, Kastin A J, Murphy S, 1976, "Hormones and regional brain blood flow", Pharnacik Biochem Rev 5 (suppl 1): 165-169; Ohkura T, Teshima Y, Isse K, Mastuda H, Inoue T, Sakai Y, Iwasaki N, Yaoi Y, 1995, "Estrogen increases cerebral and cerebellar blood flows in postmenopausal women", Menopause: J North Am Menopause Soc 2:13-18) and neuronal cell activities (Singh M, Meyer E M, Simpkins J W, 1995, "The effect of ovariectomy and estradiol replacement on brain-derived neurotrophic factor messenger ribonucleic acid expression in cortical and hippocampal brain regions of female Sprague-Dawley rats", Endocrinology 136: 4120-4124; McMillan P J, Singer C A, Dorsa D M, 1996, "The effects of ovariectomy and estrogen replacement on trkA and choline acetyltransferase mRNA expression in the basal forebrain of the adult female Sprague-Dawley rat", Neurosci 16:1860-1865).

Even though the beneficial effects of estrogen replacement on a wide variety of organ systems and tissues appear indisputable, the dose and duration of estrogen therapy is also associated with an increased risk of endometrial hyperplasia and carcinoma. The use of concomitant cyclic progestins does reduce the risk of endometrial pathology, but this is achieved at the expense of the return of regular uterine bleeding, a result that is objectionable to many patients. In addition to estrogen's stimulatory effect on the endometrium, there remains considerable controversy regarding reports of an association between long-term estrogen replacement and an increased risk of breast cancer (Bergkvist L, Adami H O, Persson I, Hoover R, Schairer C, 1989, "The risk of breast cancer after estrogen and estrogen-progestin replacement", N Eng J Med, 321:293-297; Coiditz G A, Hankinson S E, Hunter D J, Willett W X, Manson J E, Stampfer M J, Hennekens C, Rosner B, Speizer F E, 1995, "The use of estrogens and progestins and the risk of breast cancer in postmenopausal women", N Eng J Med 332:1593). Furthermore, there are other side effects of estrogen replacements, which, while might not be life threatening, contraindicate estrogen's use and reduce patient compliance.

Breast cancer is by far the most common malignant disease in women (22% of all new cancer cases). Concerted efforts are being made worldwide to develop new and safer drugs for the treatment of breast cancer. Tamoxifen ('Nolvadex'), a selective estrogen receptor modulator (SERM), is currently the most widely used drug for the treatment of estrogen receptor positive (ER+ve) breast cancer. Tamoxifen inhibits the estrogen-dependent growth of cancer cells by competitive binding to estrogen receptors of the cells. However, as tamoxifen has also estrogen-like effects, it induces, among other adverse effects, endometrial cancer, deep vein thrombosis and pulmonary embolism in women undergoing the therapy. In addition, tamoxifen is known to induce DNA adduct formation and produced liver tumors in rodent life-term bioassays. Thus there is an urgent need for developing safer SERMs for the treatment of breast cancer (Baum M, Odling-Smee W, Houghton J, Riley D, Taylor H, 1994, "Endometrial cancer during tamoxifen treatment", Lancet 343:1291; Clemons M, Danson S, Howell A, 2002, "Tamoxifen ('Nolvadex'): Antitumour treatment. A review", Cancer Treatment Reviews 28:165-180; Huggins, C, Yang N C, 1962, "Induction and extinction of mammary cancer", Science 137:257-262; Williams G M, Latropoulos, M J, Djordjevic M V, Kaltenberg O P, 1993, "The triphenylethylene drug tamoxifen is a strong liver carcinogen in the rat", Carcinogenesis 10:315-317; Meier C R, Jick H, 1998, "Tamoxifen and risk of idiopathic venous thromboembolism", Br J Clin Pharmacol 45:608-612).

Egg-implantation in most mammals is dependent on a sequential action of estrogen and progesterone on the uterus and is considered as a preferential peripheral site for contraception. Development of hormone antagonists (both antiestrogens and antiprogestins) which inhibit action of endogenous hormones at the receptor level resulting in inhibition of implantation is one of the promising approaches for control or regulation of fertility in humans and other animals. Previous studies have revealed that administration of estrogen antagonists, recently termed as Selective Estrogen Receptor Modulators (SERMs), due to their tissue selective action) to cyclic or mated females prevents implantation. Studies also reveal their uterine specific action, inhibiting endometrial receptivity to embryonic signal(s) for decidualisation, without affecting pre-implantation development of embryos up to the blastocyst stage (Singh M M, 2001, "Centchroman, a selective estrogen receptor modulator, as contraceptive and in the management of hormone related clinical disorders", Medicinal Research Reviews 21:302-347; Nityanand S, Chandravati, Singh L, Srivastava J S, Kamboj V P, 1988, "Clinical evaluation of centchroman: A new oral contraceptive", In: Hormone Antagonists for Fertility Regulation, Eds Puri C P, Van Look PFA, Indian Society for the Study of Reproduction and Fertility, Bombay, India, 241-410; Puri V, Kamboj V P, Chandra H, Ray S, Kole P L, Dhawan B N, Anand N, 1988, "Results of multicentric trial of centchroman", In: Pharmacology for Health in Asia, Eds Dhawan B N, Agarwal K K, Arora R B, Parmar S S, Allied Publishers, New Delhi, 441-447; Nityanand S, Kamboj V P, Chandravati, Das K, Gupta K, Rohtagi P, Baveja R, Jina R, Mitra R, Sharma U, 1994, "Contraceptive efficacy and safety of centchroman with biweekly-cum-weekly schedule", In: Current Concepts in Fertility Regulation and Reproduction, Eds Puri C P, Van Look PFA, Wiley Eastern Ltd., New Delhi, 61-68; Nityanand S, Gupta R C, Kamboj V P, Srivastava P K, Berry M, 1995, "Centchroman: Current Status as a contraceptive", Indian Progress in Family Welfare 10:26-31; Nityanand S, Anand N, 1996, "Centchroman: A nonsteroidal antifertility agent", FOGSI FOCUS, March issue: 8-10).

Such SERMs have also been successfully used for induction of ovulation in amenorrhic women under the assisted reproduction programs (Roy S N, Kumari G L, Modoiya K, Prakash V, Ray S, 1976, "Induction of ovulation in human with centchroman, a preliminary report", Fertility and Sterility 41:1108-1110) and suppression of post-partum lactation (Goodman and Gilman, The Pharmacological Basis of Therapeutics (Seventh Edition) Macmillan Publishing Company, 1985, pages 1321-1041).

From the foregoing discussion it would appear that the availability of therapies which possess the ideal pharmacological profile and could mimic the beneficial actions of estrogen on the bone, cardiovascular system and central nervous system without the undesirable side effects on uterus and breast, would essentially provide a "safe estrogen" which could dramatically influence the number of patients that would be able to benefit from estrogen replacement therapy. Therefore, in recognition of estrogen's beneficial effects on a number of body systems and disease conditions, there is a continuing need for the development of potent estrogen agonists which can selectively target different body tissues.

SUMMARY OF THE INVENTION

Accordingly, the present invention provides new compounds, pharmaceutically acceptable salts and compositions thereof and methods of using such compounds for the prevention or treatment of:

(a) estrogen deficient or deprivation state in a mammal, in particular osteoporosis, bone loss, bone formation, cardiovascular effects more particularly hyperlipidaemia, thrombosis and vasomotor system, neurodegenerative effects such as stroke, senile dementia-Alzheimer type and Parkinson disease, menopausal symptoms including hot flushes, urogenital atrophy, depression, mania, schizophrenia and the like, urinary incontinence, relief of dysmenorrhea; relief of dysfunctional uterine bleeding, an aid in ovarian development, treatment of acne and hirsutism;

(b) estrogen dependent or estrogen independent cancers such as prostatic carcinoma, cancer of breast, cancer of uterus, cancer of the cervix and cancer of the colon;

(c) an aid in ovarian development or function;

(d) control or regulation of fertility in humans and in other animals;

(e) prevention of threatened or habitual abortion;

(f) suppression of post-partum lactation;

(g) physiological disorders such as obesity, depression etc.;

(h) regulation of glucose metabolism in non-insulin dependent diabetes mellitus.

The present invention thus features a class of novel mercaptophenyl naphthyl methane derivatives having the following structural formula 1 or pharmaceutically acceptable salts or pharmaceutically acceptable compositions thereof:

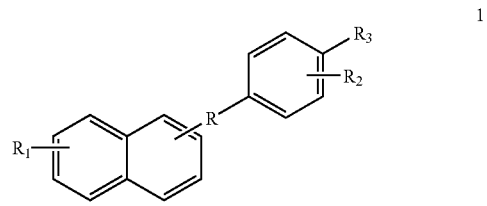

wherein R is selected from the group consisting of CO, $CH_2$ and $CHOR_4$, wherein $R_4$ is selected from the group consisting of H and $COR_5$, wherein $R_5$ is selected from the group consisting of $C_1$-$C_6$-alkyl and halo substituted $C_1$-$C_6$-alkyl, wherein $R_1$ is selected from the group consisting of H, OH, $C_1$-$C_6$-alkyl, $C_1$-$C_6$ alkyloxy and $C_1$-$C_6$ alkyloxy carbonyl, wherein $R_2$ is selected from the group consisting of H, OH, $C_1$-$C_6$ alkyl, $C_1$-$C_6$ alkyloxy and $C_1$-$C_6$ alkyloxy carbonyl, wherein $R_3$ is substituted mercapto such as $SR_6$ or $SO_2R_6$, wherein $R_6$ is selected from the group consisting of H, $C_1$-$C_6$ alkyl, aminoalkyls such as pyrrolidinoethyl, piperidinoethyl, dimethylaminoethyl and diethylaminoethyl, particularly methyl and R is CO or CHOH, $C_3$-$C_7$ cycloalkyl, $C_3$-$C_7$ heterocyclic alkyl in which the heterocycle ring is selected from the group consisting of pyrrolidinyl, pyrrolinyl, imidazolyl, imidazolidinyl, pyrazolyl, pyrazolidinyl, pyrazolinyl, piperidyl, piperazinyl, pyrrol, 2H-pyrrol, triazolyl, pyridyl, pyrazinyl, pyrimidinyl, pyridazinyl, morpholino, thiomorpholino, isothiazolyl, isozazolyl, oxazolyl, oxadiazolyl, thiadiazolyl and thiazolyl, optionally substituted with 1 to 3 substituents, independently selected from the group consisting of H, OH, halo, nitro, cyano, SH and $SO_2R_7$, wherein $R_7$ is selected from the group consisting of H, halo, $NHR_3$ and $N(R_3)_2$ wherein $R_3$ is as defined above, and halo is defined as Cl, Br and I.

The present invention also features a method for the preparation of a class of novel mercaptophenyl naphthyl methane compounds having the structural formula 1.

This invention also features pharmaceutical compositions comprising a class of novel mercaptophenyl naphthyl methane compounds having structural formula 1.

The present invention also features administration of novel derivatives of formula 1 for the prevention or treatment of symptoms of estrogen deficiency or deprivation including estrogen deficient or deprivation states in mammals, in particular osteoporosis, bone loss, bone formation, cardiovascular effects more particularly hyperlipidaemia.

The present invention thus features pharmaceutical compositions comprising a therapeutically effective amount of a compound of formula 1 or a pharmaceutically acceptable salt thereof, alone or in a combination with an estrogen or a progestin or both and one or more pharmaceutically acceptable carriers or excipients. Also featured is a novel method for the preparation of the compounds of formula 1.

The novel derivatives of formula 1 are useful for the prevention or treatment of symptoms of estrogen deficiency or deprivation including estrogen deficient or deprivation states in mammals, in particular osteoporosis, bone loss, bone formation, cardiovascular effects more particularly hyperlipidaemia.

BRIEF DESCRIPTION OF THE ACCOMPANYING FIGURES/DRAWINGS

FIG. 1. Evaluation of anti-cancer activity by in vivo effect of DMBA-induced mammary tumor in rat.

DETAILED DESCRIPTION OF BEST MODE AND SPECIFIC/PREFERRED EMBODIMENTS OF THE INVENTION

The present invention provides a class of novel mercaptophenyl naphthyl methane compounds of formula 1 or pharmaceutically acceptable salts or pharmaceutically acceptable compositions and also the administration of the compounds of formula 1 for the treatment and/or prevention of disease syndromes in animals, particularly humans related to estrogen deficiency, osteoporosis, bone loss, bone formation, cardiovascular disorders, neurodegenerative disorders, menopausal disorders, physiological disorders, diabetes disorders, prostatic carcinoma, cancer of breast, cancer of uterus, cancer of the cervix and cancer of the colon, threatened or habitual abortion, obesity, ovarian development or function, post-partum lactation and depression.

Accordingly, the present invention features novel mercaptophenyl naphthyl methane compounds having the structural formula 1,

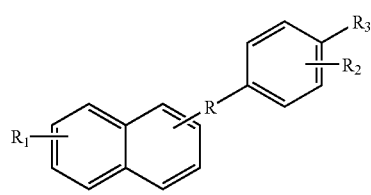

wherein R is selected from the group consisting of CO, $CH_2$ and $CHOR_4$, wherein $R_4$ is selected from the group consisting of H and $COR_5$, wherein $R_5$ is selected from the group consisting of $C_1$-$C_6$-alkyl and halo substituted $C_1$-$C_6$-alkyl, wherein $R_1$ is selected from the group consisting of H, OH, $C_1$-$C_6$-alkyl, $C_1$-$C_6$ alkyloxy and $C_1$-$C_6$ alkyloxy carbonyl, wherein $R_2$ is selected from the group consisting of H, OH, $C_1$-$C_6$ alkyl, $C_1$-$C_6$ alkyloxy and $C_1$-$C_6$ alkyloxy carbonyl, wherein $R_3$ is substituted mercapto such as $SR_6$ or $SO_2R$, wherein $R_6$ is selected from the group consisting of H, $C_1$-$C_6$ alkyl, aminoalkyls such as pyrrolidinoethyl, piperidinoethyl, dimethylaminoethyl and diethylaminoethyl, particularly methyl and R is CO or CHOH, $C_3$-$C_7$ cycloalkyl, $C_3$-$C_7$ heterocyclic alkyl in which the heterocycle ring is selected from the group consisting of pyrrolidinyl, pyrrolinyl, imidazolyl, imidazolidinyl, pyrazolyl, pyrazolidinyl, pyrazolinyl, piperidyl, piperazinyl, pyrrol, 2H-pyrrol, triazolyl, pyridyl, pyrazinyl, pyrimidinyl, pyridazinyl, morpholino, thiomorpholino, isothiazolyl, isozazolyl, oxazolyl, oxadiazolyl, thiadiazolyl and thiazolyl, optionally substituted with 1 to 3 substituents, independently selected from the group consisting of H, OH, halo, nitro, cyano SH and $SO_2R_7$, wherein $R_7$ is selected from the group consisting of H, halo, $NHR_3$ and $N(R_3)_2$, wherein $R_3$ is as defined above, and halo is defined as Cl, Br and I.

Another embodiment of the present invention features R at the C-1 position of the naphthyl ring.

Yet another embodiment of the present invention features R at the C-2 position of the naphthyl ring.

Another embodiment of the present invention features the following novel mercaptophenyl naphthyl methane compounds:

(i) (4-Methylthiophenyl)-(naphth-1-yl)-ketone;
(ii) (4-Methylsulfonylphenyl)-naphth-1-yl-ketone;
(iii) (4-Ethylsulfonylphenyl)-naphth-1-yl-ketone;
(iv) (4-Methylthiophenyl)-naphth-1-yl-carbinol;
(v) (4-Ethylthiophenyl)-naphth-1-yl-carbinol;
(vi) (4-Methylsulfonylphenyl)-naphth-1-yl-carbinol;
(vii) (4-Ethylsulfonylphenyl)-naphth-1-yl-carbinol;
(viii) 1-Piperidino-2-[(4-methylthiophenyl)-(naphth-1-yl)-methyloxy]ethane;
(ix) (4-Methylthiophenyl)-(naphth-1-yl-methanol acetate;
(x) (4-Methylthiophenyl)-1-naphthyl methylcloroacetate;
(xi) (4-Methylsulfonylphenyl)-naphth-2-yl-ketone;
(xii) (4-Methylsulfonylphenyl)-naphth-2-yl-carbinol;
(xiii) (4-Thiophenyl)-naphth-1-yl-ketone;
(xiv) (4-Ethylthiophenyl)-naphth-1-yl-ketone;
(xv) (4-Propylthiophenyl)-naphth-1-yl-ketone;
(xvi) (4-Isopropylthiophenyl)-naphth-1-yl-ketone;
(xvii) (4-Dimethylaminoethylthio-phenyl)-naphth-1-yl-ketone;
(xviii) (4-Diethylaminoethylthio-phenyl)-naphth-1-yl-ketone;
(xix) (4-Pyrrolidinoethylthio-phenyl)-naphth-1-yl-ketone; or
(xx) (4-Piperidinoethylthio-phenyl)-naphth-1-yl-ketone.

The present invention also features a method for preparing the mercaptophenyl naphthyl methane compounds of formula 1 and derivatives thereof, said method comprising the steps of:

(a) mixing α or β naphthoic acid with thioanisol or thiophenol in polyphosphoric acid at 70-120 EC for 5-10 hrs to form a compound of formula 1,

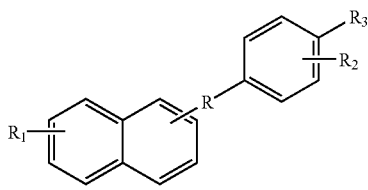

wherein R is selected from the group consisting of CO, $CH_2$ and $CHOR_4$, wherein $R_4$ is selected from the group consisting of H and $COR_5$, wherein $R_5$ is selected from the group consisting of $C_1$-$C_6$-alkyl and halo substituted $C_1$-$C_6$-alkyl, wherein $R_1$ is selected from the group consisting of H, OH, $C_1$-$C_6$-alkyl, $C_1$-$C_6$ alkyloxy and $C_1$-$C_6$ alkyloxy carbonyl, wherein $R_2$ is selected from the group consisting of H, OH, $C_1$-$C_6$ alkyl, $C_1$-$C_6$ alkyloxy and $C_1$-$C_6$ alkyloxy carbonyl, wherein $R_3$ is substituted mercapto such as $SR_6$ or $SO_2R_6$, wherein $R_6$ is selected from the group consisting of H, $C_1$-$C_6$ alkyl, aminoalkyls such as pyrrolidinoethyl, piperidinoethyl, dimethylaminoethyl and diethylaminoethyl, particularly methyl and R is CO or CHOH, $C_3$-$C_7$ cycloalkyl, $C_3$-$C_7$ heterocyclic alkyl in which the heterocycle ring is selected from the group consisting of pyrrolidinyl, pyrrolinyl, imidazolyl, imidazolidinyl, pyrazolyl, pyrazolidinyl, pyrazolinyl, piperidyl, piperazinyl, pyrrol, 2H-pyrrol, triazolyl, pyridyl, pyrazinyl, pyrimidinyl, pyridazinyl, morpholino, thiomorpholino, isothiazolyl, isozazolyl, oxazolyl, oxadiazolyl, thiadiazolyl and thiazolyl, optionally substituted with 1 to 3 substituents, independently selected from the group consisting of H, OH, halo, nitro, cyano, SH and $SO_2R_7$, wherein $R_7$ is selected from the group consisting of H, halo, $NHR_3$, $N(R_3)_2$, wherein $R_3$ is as defined above, and halo is defined as Cl, Br and I; and (b) converting the compound of formula 1 of step (a) into other derivatives by reacting the compound of formula 1 with the compounds which provide derivatives.

In another embodiment of the present invention, the derivatives of formula 1 in step (b) are obtained by reacting with haloalkane particularly iodoethane, 2-iodopropane in 5-15% NaOH under stirring for 9-18 hrs wherein R is CO, $R_1$ and $R_2$ are H and $R_3$ is S-alkyl, particularly ethyl.

In still another embodiment of the present invention, the derivatives in step (b) are obtained by reacting with ω-aminoalkyl chain, wherein R is CO, $R_1$ and $R_2$ are H and $R_3$ is ω-aminoalkoxy chain, particularly dimethyl, diethyl, pyrrolidine, piperidine.

Another embodiment of the present invention features reacting derivative of formula 1 in which R is CO, $R_1$ and $R_2$ are H and $R_3$ is S-alkyl or $SO_2$ preferably methyl, in sodium borohydride under stirring for 5-12 hrs to obtain a derivative wherein R is CO or CHOH, $R_1$=$R_2$=H and $R_3$ is S-alkyl or $SO_2$ alkyl preferably methyl.

Another embodiment of the present invention features reacting derivative of formula 1 in which is R is CO or CHOH, $R_1$ and $R_2$ are H and $R_3$ is S-alkyl, preferably methyl, with hydrogen peroxide in acetic acid under stirring for 8-10 hrs to obtain a derivative of formula 1 wherein R is CO or CHOH, $R_1$=$R_2$=H and $R_3$ is $SO_2$ alkyl, preferably methyl.

Still another embodiment of the present invention features reacting derivative of formula 1 in which is R is CHOH, $R_1$ and $R_2$ are H and $R_3$ is S-alkyl, preferably methyl, with sodium hydride in dry benzene and refluxed for 24-30 hrs to obtain derivative of formula 1 wherein, R is =$CHOCOCH_2NC_5H_{10}$, $R_1$ and $R_2$ are H and $R_3$ is S-alkyl, more particularly methyl.

Yet another embodiment of the present invention features reacting derivative of formula 1 in which R is CHOH, $R_1$ and $R_2$ are H and $R_3$ is S-alkyl, preferably methyl, with acetic anhydride in dry pyridine to stand overnight wherein, R is=$CHOCOCH_3$, $R_1$ and $R_2$ are H and $R_3$ is S-alkyl, more particularly methyl.

Yet another embodiment of the present invention features reacting derivative of formula 1 in which R is CHOH, $R_1$ and $R_2$ are H and $R_3$ is S-alkyl, preferably methyl, with chloroacetyl chloride in tetrahydropyran and pyridine under stirring for ½ hr to 3 days when the pH changed from 8 to 3, wherein R=$CHOCOCH_2Cl$, $R_1$=H, $R_2$=H, $R_3$=SMe.

Another embodiment of the present invention features pharmaceutical compositions for the treatment and/or prevention of disease syndromes in animals, particularly humans related to estrogen deficiency, osteoporosis, bone loss, bone formation, cardiovascular disorders, neurodegenerative disorders, menopausal disorders, physiological disorders, diabetes disorders, prostatic carcinoma, cancer of breast, cancer of uterus, cancer of the cervix and cancer of the colon, threatened or habitual abortion, obesity, ovarian development or function, post-partum lactation and depression, said compositions comprising effective amounts or dosage of novel mercaptophenyl naphthyl methane compounds having the structural formula 1,

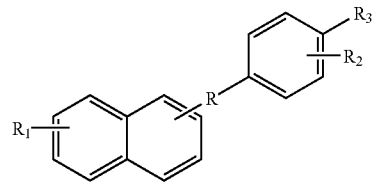

wherein R is selected from the group consisting of CO, $CH_2$ and $CHOR_4$, wherein $R_4$ is selected from the group consisting of H and $COR_5$, wherein $R_5$ is selected from the group consisting of $C_1$-$C_6$-alkyl and halo substituted $C_1$-$C_6$-alkyl, wherein $R_1$ is selected from the group consisting of H, OH, $C_1$-$C_6$-alkyl and $C_1$-$C_6$ alkyloxy, $C_1$-$C_6$ alkyloxy carbonyl, wherein $R_2$ is selected from the group consisting of H, OH, $C_1$-$C_6$ alkyl, $C_1$-$C_6$ alkyloxy and $C_1$-$C_6$ alkyloxy carbonyl, wherein $R_3$ is substituted mercapto such as $SR_6$ or $SO_2R_6$, wherein $R_6$ is selected from the group consisting of H, $C_1$-$C_6$ alkyl, aminoalkyls such as pyrrolidinoethyl, piperidinoethyl, dimethylaminoethyl and diethylaminoethyl, particularly methyl, and R is CO or CHOH, $C_3$-$C_7$ cycloalkyl, $C_3$-$C_7$ heterocyclic alkyl in which the heterocycle ring is selected from the group consisting of pyrrolidinyl, pyrrolinyl, imidazolyl, imidazolidinyl, pyrazolyl, pyrazolidinyl, pyrazolinyl, piperidyl, piperazinyl, pyrrol, 2H-pyrrol, triazolyl, pyridyl, pyrazinyl, pyrimidinyl, pyridazinyl, morpholino, thiomorpholino, isothiazolyl, isozazolyl, oxazolyl, oxadiazolyl, thiadiazolyl and thiazolyl, optionally substituted with 1 to 3 substituents, independently selected from the group consisting of H, OH, halo, nitro, cyano, SH and $SO_2R_7$, wherein $R_7$ is selected from the group consisting of H, halo, $NHR_3$ and $N(R_3)_2$, wherein $R_3$ is as defined above, and halo is defined as Cl, Br and I.

Another embodiment of the present invention features a method for treatment and/or prevention of disease syndromes related to estrogen deficiency, osteoporosis, bone loss, bone formation, cardiovascular disorders, neurodegenerative disorders, menopausal disorders, physiological disorders, diabetes disorders, prostatic carcinoma, cancer of breast, cancer of uterus, cancer of the cervix and cancer of the colon, threatened or habitual abortion, obesity, ovarian development or function, post-partum lactation and depression in mammals, including humans, by administering pharmaceutical effective dosage amounts of novel mercaptophenyl naphthyl methane compounds having the structural formula 1

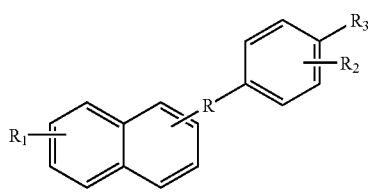

1 wherein R is selected from the group consisting of CO, $CH_2$ and $CHOR_4$, wherein $R_1$ is selected from the group consisting of H and $COR_5$, wherein $R_5$ is selected from the group consisting of $C_1$-$C_6$-alkyl and halo substituted $C_1$-$C_6$-alkyl, wherein $R_1$ is selected from the group consisting of H, OH, $C_1$-$C_6$-alkyl and $C_1$-$C_6$ alkyloxy, $C_1$-$C_6$ alkyloxy carbonyl, wherein $R_2$ is selected from the group consisting of H, OH, $C_1$-$C_6$ alkyl, $C_1$-$C_6$ alkyloxy and $C_1$-$C_6$ alkyloxy carbonyl, wherein $R_3$ is substituted mercapto such as $SR_6$ or $SO_2R_6$, wherein $R_6$ is selected from the group consisting of H, $C_1$-$C_6$ alkyl, aminoalkyls such as pyrrolidinoethyl, piperidinoethyl, dimethylaminoethyl and diethylaminoethyl, particularly methyl, and R is CO or CHOH, $C_3$-$C_7$ cycloalkyl, $C_3$-$C_7$ heterocyclic alkyl in which the heterocycle ring is selected from the group consisting of pyrrolidinyl, pyrrolinyl, imidazolyl, imidazolidinyl, pyrazolyl, pyrazolidinyl, pyrazolinyl, piperidyl, piperazinyl, pyrrol, 2H-pyrrol, triazolyl, pyridyl, pyrazinyl, pyrimidinyl, pyridazinyl, morpholino, thiomorpholino, isothiazolyl, isozazolyl, oxazolyl, oxadiazolyl, thiadiazolyl and thiazolyl, optionally substituted with 1 to 3 substituents, independently selected from the group consisting of H, OH, halo, nitro, cyano, SH and $SO_2R_7$, wherein $R_7$ is selected from the group consisting of H, halo, $NHR_3$ and $N(R_3)_2$, wherein $R_3$ is as defined above, and halo is defined as Cl, Br and I, optionally together with pharmaceutical acceptable inorganic salts, diluents, glidants, lubricants, excipients, sweetening agents, wetting agents absorbents or retardants Another embodiment of the present invention features compounds useful for the prevention or treatment of disease syndromes in animals, particularly humans related to estrogen deficiency, osteoporosis, bone loss, bone formation, cardiovascular disorders, neurodegenerative disorders, menopausal disorders, physiological disorders, diabetes disorders, prostatic carcinoma, cancer of breast, cancer of uterus, cancer of the cervix and cancer of the colon, threatened or habitual abortion, obesity, ovarian development or function, post-partum lactation and depression.

Still another embodiment of the present invention features pharmaceutical compositions that may be administered with pharmaceutical acceptable salts through oral, systemic, local or topical delivery, intravenous, intra-arterial, intra-muscular, subcutaneous, intra-peritoneal, intra-dermal, buccal, intranasal, inhalation, vaginal, rectal, transdermal or any other suitable means in any conventional liquid or solid dosage form to achieve, conventional delivery, controlled delivery or targeted delivery, optionally along with pharmaceutical acceptable diluents, excipients, glidants, lubricants, sweetening agents, wetting agents, absorbents or retardants.

Yet another embodiment of the present invention features compositions that may be delivered through gelatin capsules or compressed into tablets or pills or may be formulated in the form of lozenges, inclusion complexes with cyclodextrin derivatives, injectable depo formulations, aerosols, granules, powders, oral liquids, mucosal adhesive formulations, gel formulations, troches, elixirs, suspensions, syrups, wafers, liposomal delivery systems, implants, suppository, pessary, microemulsions, nanoemulsion, microparticles, nanoparticles, controlled release delivery systems, transdermal delivery systems, targeted delivery systems such as conjugates with monoclonal antibodies or with other suitable carrier moieties.

Another embodiment of the present invention features pharmaceutical acceptable salts of the compounds of formula 1 selected from the group consisting of formate, acetate, phenyl acetate, trifluroacetate, acrylate, ascorbate, benzoate, chlorobenzoates, bromobenzoates, iodobenzoates, nitrobenzoates, hydroxybenzoates, alkylbenzoates, alkyloxybenzoates, alkoxycarbonylbenzoates, naphthalene-2 benzoate, butyrates, phenylbutyrates, hydroxybutyrates, caprate, caprylate, cinnamate, mandelate, mesylate, citrate, tartarate, fumarate, heptanoate, hippurate, lactate, malate, maleate, malonate, nicotinate, isonicotinate, oxalate, phthalate, terephthalate, phosphate, monohydrogen phosphate, dihydrogen phosphate, metaphosphate, pyrophosphate, propiolate, propionate, phenylpropionate, salicylate, sebacte, succinate, suberate, sulfate, bisulfate, pyrosulfate, sulfite, bisulfate, sulfonate, benzene sulfonate, bromobenzene sulfonates, chlorobenzene sulfonates, ethane sulfonates, methane sulfonates, naphthalene sulfonates, toluene sulfonates, and compounds thereof.

Another embodiment of the present invention relates to the pharmaceutical acceptable diluents of the subject derivatives wherein said pharmaceutical acceptable diluents are selected from the group consisting of a lactose, mannitol, sorbitol, microcrystalline cellulose, sucrose, sodium citrate, dicalcium phosphate, or any other ingredient of the similar nature alone or in a suitable combination thereof; binder selected from the group consisting of gum tragacanth, gum acacia, methyl cellulose, gelatin, polyvinyl pyrrolidone, starch or any other ingredient of the similar nature alone or in a suitable combination thereof; excipients selected from the group consisting of agar-agar, calcium carbonate, sodium carbonate, silicates, alginic acid, corn starch, potato tapioca starch, primogel or any other ingredient of the similar nature alone or in a suitable combination thereof; lubricants selected from the group consisting of a magnesium stearate, calcium stearate or steorotes, talc, solid polyethylene glycols, sodium lauryl sulfate or any other ingredient of the similar nature alone; glidants selected from the group consisting of colloidal silicon dioxide or any other ingredient of the similar nature alone or in a suitable combination thereof; a sweetening agent selected from the group consisting of such as sucrose, saccharin or any other ingredient of the similar nature alone or in a suitable combination thereof; a flavoring agent selected from the group consisting of peppermint, methyl salicylate, orange flavor, vanilla flavor, or any other pharmaceutically acceptable flavor alone or in a suitable combination thereof; wetting agents selected from the group consisting of acetyl alcohol, glyceryl monostearate or any other pharmaceutically acceptable flavor alone or in a suitable combination thereof; absorbents selected from the group consisting of kaolin, bentonite clay or any other pharmaceutically acceptable flavor alone or in a suitable combination thereof; retarding agents selected from the group consisting of wax, paraffin or any other pharmaceutically acceptable flavor alone or in a suitable combination thereof.

One more embodiment of the present invention relates to effective administration of the pharmaceutical dosage of the subject derivatives wherein said pharmaceutical dosage of the derivatives is in the range of about 0.1 mg to 1000 mg.

One more embodiment of the present invention relates to effective administration of the pharmaceutical dosage of the subject derivatives wherein said pharmaceutical dosage of the derivatives is in the range of about 0.5 mg to 500 mg.

One more embodiment of the present invention relates to effective administration of the pharmaceutical dosage of the subject derivatives wherein said pharmaceutical dosage of the derivatives is in the range of about 1 mg to 100 mg.

One more embodiment of the present invention relates to effective administration of the pharmaceutical dosage of the subject derivatives wherein said pharmaceutical dosage of the derivatives is administered weekly, bi-weekly, daily or twice a day or three times a day or in still more divided doses.

Another embodiment of the present invention relates to the subject derivatives wherein the antiosteoporosis (antiresorptive) activity of the said derivatives as represented by T/C values is in the range of about 0.1 to 0.8.

Another embodiment of the present invention relates to the subject derivatives wherein the antiosteoporosis (antiresorptive) activity of the said derivatives as represented by T/C values is in the range of about 0.3 to 0.6.

One more embodiment of the present invention relates to compositions to enhance the bone mineral density (BMD) in the range of about 3-30%.

Yet another embodiment of the present invention relates to the subject derivatives wherein the said derivatives enhance the bone mineral Density (BMD) in the range of about 3.7-25%.

One more embodiment of the present invention relates to the subject derivatives wherein said derivatives enhance the total concentration of blood serum cholesterol by about 30%.

Another embodiment of the present invention relates to the subject derivatives wherein said derivatives enhance the total concentration of blood serum cholesterol by about 21%.

Yet another embodiment of the present invention relates to administration of the subject derivatives wherein said derivatives reduce the tumor growth by about 30%.

Another embodiment of the present invention relates to administration of the subject derivatives to reduce tumor growth by about 25%.

Another embodiment of the present invention relates to administration of the subject derivatives to enhance uterine weight in the range of about 12-45%.

Another embodiment of the present invention relates to administration of the subject derivatives to enhance uterine weight in the range of about 16-41%.

Still another embodiment of the present invention relates to administration of the subject derivatives to enhance uterine morphometry (i.e., Uterus and Endometrium) in the range of about 0.05 to 1.5 mm$^2$.

One more embodiment of the present invention relates to administration of the subject derivatives to enhance uterine morphometry (i.e., Uterus and Endometrium) in the range of about 0.80 to 1.38 mm$^2$.

Another embodiment of the present invention relates to administration of the subject derivatives to lower the relative binding affinity (RBA) to estrogen receptors by about <0.001.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES

Example 1

(4-Methylthiophenyl)-(naphth-1-yl)-ketone (1: R=CO, R$_1$=H, R$_2$=H, R$_3$=SMe)

A mixture of 1-naphthoic acid (10 g, 58.08 mmol), thioanisol (8.19 ml, 69.7 mmol) and polyphosphoric acid (100 g) was heated for 12 hours on water bath at 80° C. Reaction mixture was poured onto ice water and extracted with ethylacetate. The organic layer was washed with water, dried over anhydrous sodium sulfate and concentrated to give oil, which was crystallized from methanol to give the desired compound.

Yield: 11.5 g (71.15%), m.p.: 65° C.

IR (KBr, cm$^{-1}$): 1647 (C=O), 1506, 1550, 1585 (ArH), 650, 1025 (C—S).

$^1$H NMR (CDCl$_3$): 2.5 (s, 3H, MeS), 7.41-7.25 (dd, 2H, ArH), 7.41 (dd, 2H, ArH), 7.47-8.01 (m, 7H, naphth).

Analysis: (C$_{18}$H$_{10}$OS), Calcd: C, 77.69%; H, 5.03%, Obsd: C, 78.10%; H, 4.99%, Mass: m/z 418.

Example 2

(4-Methylsulfonylphenyl)-naphth-1-yl-ketone (1: R=CO, R$_1$=H, R$_2$=H, R$_3$=SO$_2$Me)

A mixture of (4-methylthiophenyl)-naphth-1-yl-ketone (1 g, 3.59 mmol), hydrogen peroxide (41 ml, 743.6 mmol) in acetic acid (5 ml) was stirred for 10 hours. Reaction mixture was poured onto water and extracted with ethylacetate. The organic layer was washed with water, dried over anhydrous sodium sulfate and concentrated to give oil, which was crystallized from methanol.

Yield: 0.7 g (62.77%), m.p.: 150° C.

IR (KBr, cm$^{-1}$): 678, 1109, 1416 (sulfone), 1508, 1583, (ArH), 1664 (C=O).

$^1$H NMR (CDCl$_3$): 3.06 (s, 3H, MeSO$_2$), 7.2 (dd, 2H, ArH), 7.4 (dd, 2H, ArH), 7.5-8.1 (m, 7H, naphth).

Analysis: (C$_{18}$H$_{10}$O$_2$S), Cald: C, 69.68%; H, 4.52%, Obsd: C, 69.69%; H, 4.57%

Mass: m/z 310.

Example 3

(4-Methylthiophenyl)-naphth-1-yl-carbinol (1: R=CHOH, R$_1$=H, R$_2$=H, R$_3$=SMe)

Methylthiophenyl)-naphth-1-yl-ketone (10 g, 35.9 mmol) was dissolved in of methanol (100 ml), then sodium borohydride (4.5 g, 118.9 mmol) was added slowly and the reaction mixture was stirred for 6 hours. Then methanol was distilled off and the reaction mixture was extracted with ethylacetate. The organic layer extract was washed with water, dried over anhydrous sodium sulfate, and concentrated to give oil, which was crystallized from benzene-hexane to give the desired compound.

Yield: 9.0 g (89.36%), m.p.: 80° C.

IR (KBr, cm$^{-1}$): 2941 (CH), 1560, 1595, 1600 (ArH), 669, 1062, 1180 (C—S), 3400 (OH).

¹H NMR (CDCl₃): 2.45 (s, 3H, MeS), 2.5 (s, 1H, OH), 7.18-7.22 (dd, 2H, ArH), 7.30-7.34 (dd, 2H, ArH), 7.41-7.98 (m, 7H, naphth), 6.5 (s, 1H, CH), 3.8 (s, 1H, OH).
Analysis: ($C_{18}H_{16}OS$), Calcd: C, 77.10%; H, 5.71%, Obsd: C, 77.19%; H, 5.84%.
Mass: m/z 280.

Example 4

(4-Methylsulfonylphenyl)-naphth-1-yl-carbinol (1: R=CHOH, $R_1$=H, $R_2$=H, $R_3$=SO₂Me)

A mixture of (4-methylthiophenyl)-naphth-1-yl-carbinol (1 g, 3.57 mmol) hydrogen peroxide (20 ml 646.67 mmol) in acetic acid (5 ml) was stirred for 15 hours. Then solvent was distilled off and the reaction mixture was extracted with ethylacetate. The organic layer was washed with water, dried over anhydrous sodium sulfate and concentrated to give oil, which was crystallized from benzene-hexane to give the desired compound.
Yield: 0.6 g (59.85%), m.p.: 160° C.
IR (KBr, cm⁻¹): 1109 (MeSO₂), 2941 (CH), 1081, 1510, 1598, (ArH), 673, 1109, 1311 (sulfone), 3484 (OH).
¹H NMR (CDCl₃): 3.01 (s, 3H, MeSO₂), 3.5 (s, 1H, OH), 7.25 (dd, 2H, ArH), 7.35 (dd, 2H, ArH), 7.45-8.05 (m, 7H, naphth), 6.47 (s, 1H, CH).
Analysis: ($C_{18}H_{16}O_2S$), Calcd: C, 69.41%; H, 5.13%, Obsd: C, 69.41%; H, 5.11%,
Mass: m/z 312.

Example 5

(1-Piperidino-2-[(4-methylthiophenyl)-(naphth-1-yl)-methyloxy]ethane (1: R=CHOCH₂CH₂NC₅H₁₀, $R_1$=H, $R_2$=H, $R_3$=SMe)

To a suspension of sodium hydride (0.09 g, 3.84 mmol) in dry benzene (15 ml), (4-methylthiophenyl)-naphth-1-yl-carbinol (0.3 g, 1.07 mmol) was added. The contents were refluxed for 10 minutes and then N-[2-chloroethyl]-piperidine hydrochloride (0.4 g, 2.17 mmol) was added. The reaction mixture was refluxed for 24 hours and neutralized by ethyl alcohol and concentrated. The concentrate was extracted with ethyl acetate. The organic extract was washed with water and dried over anhydrous sodium sulfate and concentrated to give oil, which was purified by column chromatography on basic alumina by using benzene-hexane as eluent to yield the desired product.
Yield: 0.11 g (26.26%).
IR (Neat, cm⁻¹): 1078, 1510, 1593, 1602 (ArH), 667, 1095 (C—S), 1217 (C—O), 2934 (CH), 3418 (amine).
¹H NMR (CDCl₃): 7.41-7.26 (dd, 2H, ArH), 7.28-7.30 (dd, 2H, ArH), 7.41-7.50 (m, 4H, naphth), 7.52-7.59 (dd, 1H, naphth), 7.83-7.85 (dd, 1H, naphth), 7.86-7.87 (dd, 1H, naphth), 6.02 (s, 1H, CH), 2.4 (s, 3H, MeS).
Analysis: ($C_{25}H_{29}OSN$), Cald: C, 76.73%; H, 7.42%, Obsd: C, 76.01%; H, 7.49%,
Mass: m/z 411.

Example 6

(4-Methylthiophenyl)-(naphth-1-yl-methanol acetate (1: R=CHOCOCH₃, $R_1$=H, $R_2$=H, $R_3$=SMe)

A mixture of (4-methylthiophenyl)-naphth-1-yl-carbinol (0.15 g, 0.54 mmol) and acetic anhydride (1 ml, 10.6 mmol) was taken in dry pyridine (4 ml). Reaction mixture was allowed to stand for overnight, poured onto ice-cold water and extracted with ethylacetate. The organic extract was washed with water and dried over anhydrous sodium sulfate and concentrated to give the desired product as oil.
Yield: 0.111 g (64.35%).
IR (Neat, cm⁻¹): 1033, 1096, 1598, 1596 (ArH), 667, 1020, 1091 (C—S), 2925 (CH), 1737 (ester).
¹H NMR (CDC₁₃): 7.1-7.95 (m, 11H, ArH), 2.17 (s, 3H, CH₃), 2.43 (s, 3H, MeS), 6.21 (s, 1H, CH).
Analysis: ($C_{20}H_{18}O_2S$), Cald: C, 74.59%; H, 5.59%, Obsd: C, 74.51%; H, 5.55%,
Mass: m/z 322.

Example 7

(4-Methylthiophenyl)-1-naphthyl methylchloroacetate (1: R=CHOCOCH₂Cl, $R_1$=H, $R_2$=H, $R_3$=SMe)

A mixture of (4-methylthiophenyl)-naphth-1-yl-carbinol (0.15 g, 0.54 mmol), THF (3 ml) was stirred at 0 EC. To this stirred solution chloroacetyl chloride (0.6 ml, 7.59 mmol) was added drop wise. After 1 hr. dry pyridine (1.5 ml) was added and the stirring was continued for 2 days at room temperature. Reaction mixture was decomposed with cold water. Extracted with ethylacetate. The organic layer was washed with 5% HCl solution and then finally with water, dried over anhydrous sodium sulfate. Ethylacetate was concentrated to give oil, which was crystallized with benzene and hexane to give the desired product.
Yield: 0.9 g (47.12%). IR (Neat, cm⁻¹): 1094, 1598 (ArH), 2941 (CH), 669, 1089 (C—S), 1724 (ester), 849 (C—Cl).
¹H NMR (CDCl₃): 7.16-8.02 (m, 11H, ArH), 2.44 (s, 3H, MeS), 5.87 (s, 1H, CH), 3.45 (s, 2H, CH₂Cl).
Mass: m/z 321 [M⁺-36].

Example 8

(4-Methylsulfonylphenyl)-naphth-2-yl-ketone (1: R=CO, $R_1$=H, $R_2$=H, $R_3$=SO₂Me)

A mixture of (4-methylthiophenyl)-naphth-2-yl-ketone (1 g, 3.59 mmol), hydrogen peroxide (41 ml, 743.6 mmol) in acetic acid (5 ml) was stirred for 10 hours reaction mixture was poured onto water and extracted with ethylacetate. The organic layer was washed with water, dried over anhydrous sodium sulfate and concentrated to give oil, which was crystallized from methanol.
Yield: 0.5 g (44.84%), m.p.: 160° C.
IR (KBr, cm⁻¹): 1109, 1298, 1416 (sulfone), 1066, 1598 (ArH), 1684 (C=O).
¹H NMR (CDCl₃): 3.10 (s, 3H, MeSO₂), 7.25-8.72 (m, 11H, ArH)
Analysis: ($C_{18}H_{10}O_2S$), Cald: C, 69.68%; H, 4.52%, Obsd: C, 69.79%; H, 4.59%
Mass: m/z 310.

Example 9

(4-Methylsulfonylphenyl)-naphth-2-yl-carbinol (1: R=CHOH, $R_1$=H, $R_2$=H, $R_3$=SO₂Me)

A mixture of (4-methylthiophenyl)-naphth-2-yl-carbinol (1 g, 3.57 mmol) hydrogen peroxide (20 ml, 446.6 mmol) in acetic acid (5 ml) was stirred this reaction mixture for 15 hours Then solvent was distilled off and the reaction mixture was extracted with ethylacetate. The organic layer was washed with water, dried over anhydrous sodium sulfate and concentrated to give oil, which was crystallized from benzene-hexane to give the desired compound.

Yield: 0.7 g (62.82%), m.p.: 100° C.

IR (KBr, cm$^{-1}$): 1106, 1298 (sulfone), 1003, 1574, 1608 (ArH), 3413 (OH).

$^1$H NMR (CDCl$_3$): 3.02 (s, 3H, MeSO$_2$), 3.7 (s, 1H, OH), 7.26-7.93 (m, 11H, ArH), 6.08 (s, 1H, CH).

Analysis: (C$_{18}$H$_{16}$O$_2$S), Calcd: C, 69.41%; H, 5.13%, Obsd: C, 69.41%; H, 5.11%, Mass: m/z 312.

Example 10

(4-Thiophenyl)-naphth-1-yl-ketone (1: R=CO, R$_1$=H, R$_2$=H, R$_3$=SH)

A mixture of 1-naphthoic acid (8 g, 46.46 mmol), thiophenol (8 ml, 78.05 mmol) and polyphosphoric acid (80 g) was heated for 12 hours on water bath at 80 EC. Reaction mixture was poured onto ice water and extracted with ethylacetate. The organic layer was washed with water, dried over anhydrous sodium sulfate and concentrated to give oil, which was crystallized from methanol to give the desired compound.

Yield: 6.5 g (52.94%), m.p.: 50° C.

IR (KBr, cm$^{-1}$): 1683 (C=O), 1084, 1507, 1592 (ArH), 4160 (SH).

$^1$H NMR (CDCl$_3$): 3.3 (s, 1H, SH), 7.18-8.48 (m, 11H, ArH), Mass: m/z 264.

Example 11

(4-Ethylthiophenyl)-naphth-1-yl-ketone (1: R=CO, R$_1$=H, R$_2$=H, R$_3$=SC$_2$H$_5$)

A mixture of (4-thiophenyl)-naphth-1-yl-ketone (0.2 g, 0.76 mmol), iodoethane (0.7 ml, 7.4 mmol) in 10% NaOH (5 ml) was stirred for 12 hours Reaction mixture was extracted with ethylacetate. The organic layer was washed with water, dried over anhydrous sodium sulfate and concentrated to give the desired compound as oil.

Yield: 0.15 g (67.81%).

IR (Neat, cm$^{-1}$): 665, 773 (C—S), 1677 (C=O), 1415, 1595 (ArH).

$^1$H NMR (CDCl$_3$): 7.25-9.10 (m, 11H, ArH), 1.25 (t, 3H, CH$_2$CH$_3$), 3.3 (q, 2H, CH$_2$CH$_3$), Mass: m/z 292.

Example 12

(4-Isopropylthiophenyl)-naphth-1-yl-ketone (1: R=CO, R$_1$=H, R$_2$=H, R$_3$=SCH(CH$_3$)$_2$ A mixture of (4-thiophenyl)-naphth-1-yl-ketone 1-naphthoic acid (0.2 g, 0.76 mmol), 2-iodopropane (0.8 ml, 8 mmol) in 10% NaOH (5 ml) was stirred for 12 hours. Reaction mixture was extracted with ethylacetate. The organic layer was washed with water, dried over anhydrous sodium sulfate and concentrated to give the desired compound as oil.

Yield: 0.10 g (60.41%).

IR (Neat, cm$^{-1}$): 668, 849 (C—S), 1668 (C=O), 1041, 1582 (ArH).

$^1$H NMR (CDCl$_3$): 7.26-9.10 (m, 11H, ArH), 1.25 (d, 6H, CH(CH$_3$)$_2$), 3.5 (m, $^1$H CH(CH$_3$)$_2$), Mass: m/z 306.

Example 13

(4-Dimethylaminoethylthio-phenyl)-naphth-1-yl-ketone (1: R=CO, R$_1$=H, R$_2$=H, R$_3$=SCH$_2$CH$_2$NMe$_2$)

A mixture of (4-thiophenyl)-naphth-1-yl-ketone (0.2 g, 0.76 mmol), 2-[dimethylamino]-ethylchloride hydrochloride (0.2 g, 1.38 mmol) and anhydrous potassium carbonate (0.6 g, 4.34 mmol) in dry acetone (15 ml) was refluxed for 18 hours. Potassium carbonate was filtered off. Acetone was distilled off. Reaction mixture was extracted with ethylacetate, washed with water and dried over anhydrous sodium sulfate and concentrated to give oil. Reaction mixture was passed through basic alumina column using hexane-benzene as eluent to yield desired product as oil.

Yield: 0.12 g (47.28%).

IR (Neat, cm$^{-1}$): 667, 847 (C—S), 1038, 1500, 1579 (ArH), 1701 (C=O), 3441 (amine), Mass: m/z 335.

Example 14

(4-Diethylaminoethylthio-phenyl)-naphth-1-yl-ketone (1: R=CO, R$_1$=H, R$_2$=H, R$_3$=SCH$_2$CH$_2$NEt$_2$)

A mixture of (4-thiophenyl)-naphth-1-yl-ketone (0.2 g, 0.76 mmol), 2-[diethylamino]-ethylchloride hydrochloride (0.2 g, 1.16 mmol), and anhydrous potassium carbonate (0.6 g, 4.34 mmol) in dry acetone (15 ml) was refluxed for 18 hours. Potassium carbonate was filtered off. Acetone was distilled off. Reaction mixture was extracted with ethylacetate, washed with water and dried over anhydrous sodium sulfate and concentrated to give oil. Reaction mixture was passed through basic alumina column using hexane-benzene as eluent to yield desired product as oil.

Yield: 0.155 g (56.36%).

IR (Neat, cm$^{-1}$): 666, 847 (C—S), 1072, 1500, 1583 (ArH), 1702 (C=O), 3430 (amine), Mass: m/z 335.

Example 15

(4-Pyrrolidinoethylthio-phenyl)-naphth-1-yl-ketone (1: R=CO, R$_1$=H, R$_2$=H, R$_3$=SCH$_2$CH$_2$NC$_4$H$_8$)

A mixture of (4-thiophenyl)-naphth-1-yl-ketone (0.2 g, 0.76 mmol), anhydrous potassium carbonate (0.6 g, 4.34 mmol), N-[2-chloroethyl]-pyrrolidine hydrochloride (0.2 g, 1.17 mmol) in dry acetone (20 ml) was refluxed for 13 hours. Potassium carbonate was filtered off. Acetone was distilled off. Reaction mixture was extracted with ethylacetate, washed with water and dried over anhydrous sodium sulfate and concentrated to give oil. This oil was purified by column chromatography on basic alumina using benzene-hexane as eluent to yield the desired product.

Yield: 0.13 g (47.59%).

IR (Neat, cm$^{-1}$): 500, 1596 (ArH), 617, 786 (CS), 1703 (C=O), 3441 (amine). Mass: m/z 361.

Example 16

(4-Piperidinoethylthio-phenyl)-naphth-1-yl-ketone (1: R=CO, R$_1$=H, R$_2$=H, R$_3$=SCH$_2$CH$_2$NC$_5$H$_{10}$)

A mixture of (4-thiophenyl)-naphth-1-yl-ketone (0.2 g, 0.76 mmol), anhydrous potassium carbonate (0.6 g, 4.34 mmol), N-[2-chloroethyl]-piperidine hydrochloride (0.2 g, 1.09 mmol), in dry acetone (15 ml) was refluxed for 12 hours. Potassium carbonate was filtered off. Acetone was distilled off. Reaction mixture was extracted with ethylacetate, washed with water and dried over anhydrous sodium sulfate and concentrated to give oil. This oil was purified by column chromatography on basic alumina using benzene-hexane as eluent to yield the desired product.

Yield: 0.12 g (44.24%).

IR (Neat, cm$^{-1}$): 1509, 1610 (ArH), 661, 847 (C—S), 3429 (amine), 1704 (C=O). $^1$H NMR (CDCl$_3$): 7.41-8.94 (m, 11H, ArH), 4.28-4.33 (t, 2H, CH$_2$N), 4.59-4.59 (t, 2H, SCH$_2$), 1.18-1.32 (m, 6H, 3×CH$_2$ of piperidine), 2.17 (m, 4H, 2×NCH$_2$).

Mass: m/z 384.

Biological Evaluation:

The compounds of the present invention were evaluated for use for the prevention or treatment of symptoms of estrogen deficiency or deprivation including estrogen deficient or deprivation state in mammals, in particular osteoporosis, bone loss, bone formation, cardiovascular effects more particularly hyperlipidaemia, prevention or the treatment of estrogen dependent or estrogen independent cancers such as cancer of breast and control or regulation of fertility in humans and in other animals. Detailed procedures for the evaluation of the compounds of the present invention or pharmaceutically acceptable salts or compositions thereof are described hereunder:

Test Procedure for Evaluation of Antiosteoporosis (Antiresorptive) Activity in Vitro:

Test solutions of the compounds of the present invention are prepared in appropriate solvents in concentration range of 5 millimolar to 400 millimolar, most preferably in concentrations of 20 millimolar. 5 µl of each concentration are used for evaluation of antiresorptive activity in vitro. In control experiments, 5 µl of appropriate solvent is used in lieu of test compound. Femur bones are isolated from chick embryos on day 11 post-ovulation. The adhering soft connective tissue is completely removed. Each femur bone is then placed in a drop of phosphate buffered saline (PBS) and is transferred to BGJ$_b$ culture medium containing $^{45}$CaCl$_2$ and incubated for 2 h. Labeled femur bones are washed 2-3 times with PBS and transferred to BGJ$_b$ medium containing parathyroid hormone and cultured for 96 h in the presence or absence of the compound of invention or the vehicle in BGJ$_b$ medium. Contralateral femur of each fetus serves as corresponding control. Culture medium with the respective treatment in each well is changed after 48 h. On termination of the culture at 96 h, bones are transferred to 0.1 N HCl for 24 h. Radioactivity due to $^{45}$Ca in the spent medium collected at 48 and 96 h of culture and HCl extract at 96 h of culture is quantified by Liquid Scintillation Spectrophotometer in 10 ml of the scintillation fluid. Bone resorbing activity is expressed as percentage of $^{45}$Ca released into the culture medium and the effect of the compound of invention as percent of the corresponding contra-lateral control or T/C ratio as shown below:

$$T/C \text{ ratio} = \frac{^{45}Ca \text{ resorption in presence of PTH + test agent}}{^{45}Ca \text{ resorption in presence of PTH + vehicle}}$$

Appropriate solvents are selected from solvents like water, normal saline, phosphate buffered saline, phosphate buffer, DMSO alone or in a suitable combination thereof.

In accordance with the above test procedure, the compounds of the present invention, on employing or administering their effective amounts, exhibit positive response by inhibiting the PTH induced resorption of $^{45}$Ca from chick fetal bones in culture. This compound showed promising antiresorptive activity in vitro using chick foetal bone assay with T/C ratio of 0.4 to 0.8 at 25 µM to 100 µM concentrations in comparisons to Raloxifene having T/C of 0.6 (Table 1). It was devoid of any pos-coital antifertility and estrogenic activities in rats. Activity in the above test procedure indicates that the compounds of the present invention are useful as antiresorptive agents in the treatment of post-menopausal osteoporosis.

TABLE 1

Inhibition in PTH-induced resorption of $^{45}$Ca from chick fetal bones in culture:

| Example Number | Concentration in µM | T/C Ratio |
|---|---|---|
| 1 | 25 | 0.77 |
|  | 50 | 0.60 |
|  | 100 | 0.44 |
| 3 | 50 | 1.41 |
| 4 | 100 | 0.97 |
| 9 | 100 | 1.15 |
| 11 | 100 | 0.77 |

Test Procedure for Evaluation of Antiosteoporosis Activity in Vivo:

The in vivo antiosteoporosis activity is evaluated in colony-bred adult (3-4 month old) female Sprague-Dawley rats or female retired breeder Sprague-Dawley rats (12-10 months old; parity$\geq$3). Animals are bilaterally ovariectomized (OVX) under light ether anesthesia and treated with the compound of the present invention, 17-alfa-ethynylestradiol (EE) or the vehicle once daily on days 1-30 post-ovariectomy (day 1: day of bilateral ovariectomy) by the oral route. One group consisting of females is sham operated and treated similarly with the vehicle. Animals of all the groups are autopsied 24 h after the last treatment. Before autopsy, 24 h fasting urine samples are collected in fresh containers using all-glass metabolic cages and stored at −20° C. until analyzed for calcium, phosphorus and creatinine. At autopsy, about 5 ml blood samples are collected by cardiac puncture from each rat under light ether anesthesia and serum is isolated and stored at −20° C. until analyzed for total and bone specific alkaline phosphatase, osteocalcin and calcium. Uterus of each rat is carefully excised, gently blotted, weighed and fixed for histology. Representative sections (5 µm) from each uterus are stained with haematoxylin and eosin. Femur and tibia of each rat are then dissected free of adhering tissue, fixed in 70% ethanol in physiological saline and stored at −20° C. until Bone Mineral Density (BMD) measurement. Before autopsy, whole body scan of each rat for measurement of BMD is performed on an Hologic QDR-4500A fan-beam densitometer, calibrated daily with Hologic hydroxyapatite anthropomorphic spine phantom using manufacturer provided software for small animals. BMD measurement of isolated bones is performed using identical regions of interest. Serum total alkaline phosphatase, osteocalcin, calcium ion content and urinary calcium and creatinine are estimated colorimetrically using commercial kits (Table 2).

TABLE 2

Increase in BMD (g/cm$^2$): Percent of OVX + vehicle treatment group:

| | Percent Increase | |
|---|---|---|
| Region of Interest | Example Number-1 | EE |
| Femur Global | 8 | 16.1 |
| Femur Neck | 13 | 13.5 |
| Tibia Global | 3.7 | 3.8 |
| Tibia proximal | 13.8 | 25.2 |

Test Procedure for Evaluation of Anti-Hyperlipidaemic Activity:

The in vivo anti-hyperlipidaemic activity is evaluated in colony-bred adult (3-4 month old) female Sprague-Dawley rats or female retired breeder Sprague-Dawley rats (12-10 months old; parity≧3). Animals are bilaterally ovariectomized (OVX) under light ether anesthesia and treated with the compound of the present invention, 17-alfa-ethynylestradiol (EE) or the vehicle once daily on days 1-30 post-ovariectomy (day 1: day of bilateral ovariectomy) by the oral route. One group consisting of females is sham operated and treated similarly with the vehicle. Animals of all the groups are autopsied 24 h after the last treatment. At autopsy, about 5 ml blood samples are collected by cardiac puncture from each rat under light ether anesthesia and serum is isolated and stored at −20° C. until analyzed for total cholesterol. The total cholesterol concentration is measured by a timed-end point method using a Beckman Synchron CX autoanalyser. In the reaction, cholesterol estrase hydrolyses cholesterol esters to free cholesterol and fatty acids. Free cholesterol is oxidized to cholestene-3-one and $H_2O_2$ by cholesterol oxidase. Peroxidase catalyses the reaction of H2O2 with 4-amino antipyrine and phenol to produce a colored quinoneimine product. Absorbance is recorded at 520 nm (Table 3).

TABLE 3

Percent change in blood serum total cholesterol concentration:

| Treatment Group | Daily Dose (mg/kg) | Total Cholesterol (mg/dl) | % Change |
|---|---|---|---|
| Sham intact | — | 18.83 | |
| OVX + vehicle | — | 25.62 | 36.01 |
| EE | 0.50 | <5 | |
| Example number 1 | 10 | 20.00 | 21.94 |

Test Procedure for Evaluation of Antiproliferative/Cytotoxic Activity In Vitro:

The procedure is based on the following methods: New colorimetric assay for anticancer drug screening, Skehan et al., J Natn Cancer Inst, 82, 1107, 1990 and Feasibility of a high-flux anticancer drug screen using a diverse panel of cultured human tumor cell lines 83, 847, 1991.

A fully confluent flask of MCF-7 cells in trypsinized and $10^4$ cells/well are plated in a 96 welled flat bottomed plate in 200 µl Minimum Essential Medium (MEM), pH 7.4 and allowed to attach for 24 h at 37° C. in a humidified $CO_2$ incubator. Subsequently, the compound of invention dissolved in DMSO or ethanol is added at a specified concentration and further incubated for 48 h as before. The cells are then fixed in 50 µl cold 50% TCA and incubated for 1 h at 4° C. The supernatant is discarded and the plate is washed five times with deionized water and air dried. 100 µl of 0.4% (w/v) Sulforhodamine B (SRB) in 1% acetic acid is added to each well and incubated at room temperature for 30 minutes. Unbound SRB is removed by five washes with chilled 1% acetic acid and the plate is air dried. 200 µl of unbuffered 10 mM Tris base is added to solubilize the bound stain for 5 minutes at room temperature and O.D. is read at 560 nm in a plate reader. The graph is plotted between O.D. and concentration and LC50 is calculated with respect to tamoxifen, which is used as a positive control (Table 4).

TABLE 4

Antiproliferative/cytotoxic activity in cultured MCF-7 cells:

| Compound | $LC_{50}$ (µM) |
|---|---|
| Tamoxifen | 12.42 |
| Example number 1 | Inactive |

Test Procedure for Evaluation of Anti-Cancer Breast Activity In Vivo:

Compound(s) of invention identified on the basis of the above test are evaluated in vivo for anticancer breast activity using the well established and widely used rodent model of hormone responsive breast cancer namely, 7,12-dimethylbenz (a) anthracene (DMBA) induced rat mammary tumor model. Healthy female Sprague-Dawley rats (50-60 days of age) are given a single oral administration of DMBA (180 mg/kg) and the mammary tumor development is monitored by weekly palpation of the mammary tracks. Body weight of the animals is recorded weekly. All animals are used and handled adhering to the Animal Ethics Committee guidelines for humane treatment of animals. The animals have free access to standard rodent pellet diet and safe drinking water and are housed in temperature and photoperiod-controlled animal quarters throughout the experimental period. When palpable mammary tumors develop and reach approximately 0.5 cm in diameter, the tumor bearing rats are grouped and receive oral administration of the test compound at a daily dose of 10-mg/kg body weight for 4 weeks. Tumor incidence, number and area/volume are recorded at the commencement of the treatment and at weekly intervals. The diameter of tumors is measured using calipers and the tumor volume is derived using the formula for sphere volume. The compound is considered active against mammary tumor if, by the end of treatment period, the tumor volume decreases by more than 25% or remains static or when the volume shows less than 25% increase over the pre-treatment volume (FIG. 1).

Test Procedure for Evaluation of Post-Coital Antifertility Activity:

Adult female rats are caged overnight with coeval males of proven fertility and their vaginal smears are checked on the following morning. The day of presence of spermatozoa in the vaginal smear is taken as day 1 of pregnancy. Mated rats are isolated and randomized into various treatment groups and treated orally with the compound of invention or the vehicle on days 1-7/1-5 post-coitum. Animals of all the groups are autopsied on day 10 post-coitum and number and status of corpora lutea and implantation sites in each rat are recorded. The compounds of the present invention are considered active if there is complete absence of implantations in the uterus of all rats, in comparison to presence of normal implantations in the uterus of rats of vehicle control group (Table 5).

TABLE 5

Post-coital antifertility efficacy:

| Treatment Group | Daily Dose (mg/kg) | Treatment Schedule (days post-coitum) | % Efficacy |
|---|---|---|---|
| Vehicle | — | 1-7 | — |
| Example number 1 | 10 | 1-7 | — |

Test Procedure for Evaluation of Estrogen Agonistic Activity:

Twenty-one-day-old immature female rats are bilaterally ovariectomized under light ether anesthesia and, after post-operative rest for 7 days, are randomized into different treatment groups. Each rat receives the compound of the invention once daily for 3 consecutive days on days 28-30 of age. A separate group consisting of animals receiving only the vehicle for similar duration serves as control. At autopsy 24 h after the last treatment on day 31 of age, vaginal smear of each rat is taken and uterus is carefully excised, gently blotted, weighed and fixed for histology and histomorphometry using image analysis. Premature opening of vagina, cornification of vaginal epithelium, increase in uterine fresh weight, total uterine and endometrial area and uterine luminal epithelial cell height are taken as parameters for evaluation of estrogen agonistic activity in comparison to rats of vehicle control group (Table 6).

TABLE 6

Increase in uterine weight: Percent of OVX + vehicle treatment group:

| Compound | Treatment Group | Daily Dose (mg/kg) | Percent Increase |
|---|---|---|---|
| 17-alfa-Ethynylestradiol | Immature OVX rats | 0.01 | 419 |
| | Retired breeder OVX rats | 0.5 | 260 |
| Example number 1 | Immature OVX rats | 10 | 16 |
| | Retired breeder OVX rats | 10 | 41 |

For image analysis in estrogen agonistic activity evaluation studies, paraffin sections (6 μm thick) of the uterus stained with haematoxylin and eosin were analyzed microscopically. To determine changes in uterine tissue components, areas of whole uterus and endometrium and the thickness of uterine epithelium were measured using a computer-image analysis system (BioVis, Expert Vision, India). Briefly, microscopic images of uterus acquired through a CCD camera were loaded in to the image analysis program and spatially calibrated against a stage micrometer image taken at the same magnification. Using thresholding and line tools, the regions for measurements were selected and the area (mm$^2$) of whole uterine transection excluding the luminal space, the area (mm$^2$) of the endometrium only, and the thickness (μm) of luminal epithelial lining were measured. Luminal epithelial thickness data was the average of measurements made at 6 randomly selected sites of the lining (Table 7).

TABLE 7

Estrogen agonistic activity: Effect on uterine morphometry:

| Compound | Treatment Group | Daily Dose (mg/kg) | Uterus Total Area Mm$^2$ | Endometrium Total Area mm$^2$ | Endometrium Epithelial Cell Height μm |
|---|---|---|---|---|---|
| | Immature OVX rats | — | 0.29 | 0.12 | 6.36 |
| | Retired breeder OVX rats | — | 1.89 | 0.54 | 10.58 |
| 17-alfa-Ethynylestradiol | Immature OVX rats | 0.01 | 1.21 | 0.57 | 33.65 |
| | Retired breeder OVX rats | 0.5 | 6.86 | 4.07 | 46.36 |
| Example number 1 | Immature OVX rats | 10 | 0.105 | 0.085 | 7.16 |
| | Retired breeder OVX rats | 10 | 1.38 | 0.37 | 9.63 |

Test Procedure for Evaluation of Estrogen Antagonistic Activity:

Twenty-one-day-old immature female rats are bilaterally ovariectomized under light ether anesthesia and after postoperative rest for 7 days, are randomized into different treatment groups. Each rat receives the compounds of the invention and 0.02 mg/kg dose of 17-alfa-ethynylestradiol in 10% ethanol-distilled water once daily for 3 consecutive days on days 28-30 of age. A separate group consisting of animals receiving only 17-alfa-ethynylestradiol (0.02 mg/kg) in 10% ethanol-distilled water for similar duration are used for comparison. At autopsy on day 31 of age, vaginal smear of each rat is taken and uterus is carefully excised, gently blotted, weighed and fixed for histology and histomorphometry using image analysis. Inhibition in 17-alfa-ethynylestradiol-induced premature opening of vagina, cornification of vaginal epithelium, increase in uterine fresh weight, total uterine and endometrial area and uterine luminal epithelial cell height are taken as parameters for evaluation of estrogen antagonistic activity (Table 8).

TABLE 8

Percent inhibition in EE induced uterine weight gain:

| Compound | Treatment Group | Daily Dose (mg/kg) | Percent Inhibition |
|---|---|---|---|
| Example number 1 | Immature OVX rats | 10 | 32 |

Test Procedure for Evaluation of Relative Binding Affinity (RBA) to Estrogen Receptors The relative binding affinity (RBA) of the compounds for estrogen receptor was determined by competition assay, employing $^3$H-estradiol ($^3$H-E$_2$) as the radioligand. The test ligands and $^3$H-E$_2$ were incubated at 4° C. with cytosol estrogen receptors obtained from uteri of immature estradiol-primed (1 μg/rat 24 h before autopsy) 20-21 days old rats. Aliquot of uterine cytosol (200 μl; 2 uteri per ml) prepared in TEA buffer (10 mM Tris, 1.5 mM EDTA, 0.02% sodium azide, pH 7.4) were incubated in duplicate with a fixed concentration of $^3$H-E$_2$ in the absence or presence of various concentrations of the competitor substance dissolved in 30 μl of the TEA buffer containing DMF as co-solvent (final concentration of DMF in the incubation mixture never exceeded 5%) for 18 hrs at 4° C. At the end of this period, dextran coated charcoal (5% Norit 0.5% dextran) suspension in 100 μl of TEA buffer was added to each tube, which were briefly vortexed and allowed to stand for 15 minutes at 4° C. The mixture was centrifuged at 800 g for 10 minutes and the supernatants counted for radioactivity in 10 ml of a dioxane-based scintillation fluid. RBA of the text compound was computed from a graph plotted between percent bound radioactivity verses log concentration of the test substance. At 50% inhibition, log of the competitor concentration relative to that of 17-beta-estradiol, gave the affinity of the test compound to estrogen receptor relative to estradiol. This when multiplied With 100 gave the percentage value designated as RBA (Table 9).

TABLE 9

Relative binding affinity (RBA) to estrogen receptors:

| Compound | RBA |
|---|---|
| 17-beta-Estradiol | 100 |
| Example number 1 | <0.001 |

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A mercaptophenyl naphthyl methane compound having the structural formula 1:

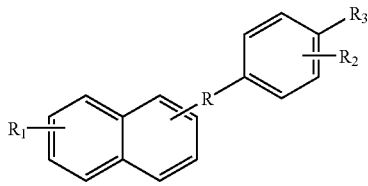

wherein R is CO at the C-1 position of the naphthyl ring, wherein $R_1$ is H, wherein $R_2$ is H, and wherein $R_3$ is substituted mercapto and is not SH.

2. A mercaptophenyl naphthyl methane compound having the structural formula 1:

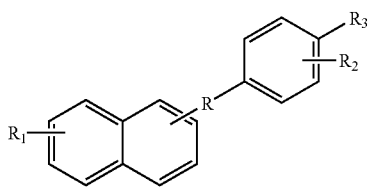

wherein R is CO at the C-1 position of the naphthyl ring, wherein $R_1$ is H, wherein $R_2$ is H, and wherein $R_3$ is $SR_6$ or $SO_2R_6$, wherein $R_6$ is selected from the group consisting of $C_1$-$C_6$ alkyl, aminoalkyl, pyrrolidinoethyl, piperidinoethyl, dimethylaminoethyl, and diethylaminoethyl.

3. A mercaptophenyl naphthyl methane compound as defined by claim 1, which is:
   (a) (4-Methylthiophenyl)-(naphth-1-yl)-ketone;
   (b) (4-Methyl sulfonylphenyl)-naphth-1-yl-ketone;
   (c) (4-Ethylsulfonylphenyl)-naphth-1-yl-ketone;
   (i) (4-Ethylthiophenyl)-naphth-1-yl-ketone;
   (j) (4-Propylthiophenyl)-naphth-1-yl-ketone;
   (k) (4-Isopropylthiophenyl)-naphth-1-yl-ketone;
   (l) (4-Dimethylaminoethylthio-phenyl)naphth-1-yl-ketone;
   (m) (4-Diethylaminoethylthio-phenyl)-naphth-1-yl-ketone;
   (n) (4-Pyrrolidinoethylthio-phenyl)-naphth-1-yl-ketone; or
   (o) (4-Piperidinoethylthio-phenyl)-naphth-1-yl-ketone.

4. A method for the preparation of a mercaptophenyl naphthyl methane compound having the structural formula 1, comprising the steps of:
   (a) mixing α naphthoic acid with thioanisol or thiophenol in polyphosphoric acid at 70-120° C. for 5-10 hrs to form a compound of formula 1,

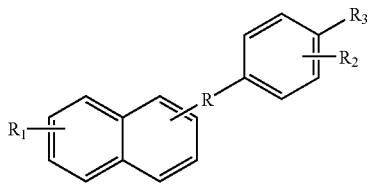

wherein R is CO at the C-1 position of the naphthyl ring, wherein $R_1$ is H, wherein $R_2$ is H, and wherein $R_3$ is substituted mercapto and is not SH, or $SR_6$ or $SO_2R_6$, wherein $R_6$ is selected from the group consisting of H, $C_1$-$C_6$ alkyl, aminoalkyl, pyrrolidinoethyl, piperidinoethyl, dimethylaminoethyl, diethylaminoethyl; and
   (b) converting the compound of formula 1 of step (a) into other derivatives by reacting said compound of formula 1 with compounds contributing said derivatives.

5. The method as defined by claim 4, wherein the derivative of formula 1 in step (b) is obtained by reaction with a haloalkane in 5-15% NaOH under stirring for 9-18 hrs, wherein in formula 1, R is CO, $R_1$ and $R_2$ are H, and $R_3$ is S-alkyl.

6. The method as defined by claim 4, comprising reacting the derivative of formula 1 in which R is CO, $R_1$ and $R_2$ are H and $R_3$ is S-alkyl or $SO_2$, in sodium borohydride under stirring for 5-12 hrs, to obtain a derivative wherein R is CO, $R_1$=$R_2$=H and $R_3$ is S-alkyl or $SO_2$ alkyl.

7. The method as defined by claim 6, comprising reacting the derivative of formula 1 in which R is CO, $R_1$ and $R_2$ are H and $R_3$ is S-alkyl, with hydrogen peroxide in acetic acid under stirring for 8-10 hrs, to obtain a derivative of formula 1 wherein R is CO, $R_1$=$R_2$=H and $R_3$ is $SO_2$ alkyl.

8. A pharmaceutical composition comprising a mercaptophenyl naphthyl methane compound having structural formula 1

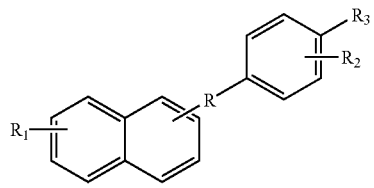

wherein R is CO at the C-1 position of the naphthyl ring, wherein $R_1$ is H, wherein $R_{12}$ is H, and wherein $R_3$ is substituted mercapto, $SR_6$ or $SO_2R_6$, wherein $R_6$ is selected from the group consisting of $C_1$-$C_6$ alkyl, aminoalkyl, pyrrolidinoethyl, piperidinoethyl, dimethylaminoethyl and diethylaminoethyl; and a pharmaceutically acceptable carrier, inorganic salt, diluent, glidant, lubricant, excipient, sweetening agent, wetting agent, absorbent and/or retardant therefor.

9. The pharmaceutical composition as defined by claim 8, comprising:
   (a) (4-Methylthiophenyl)-(naphth-1-yl)-ketone;
   (b) (4-Methylsulfonylphenyl)-naphth-1-yl-ketone;
   (c) (4-Ethyl sulfonylphenyl)-naphth-1-yl-ketone;
   (i) (4-Ethylthiophenyl)-naphth-1-yl-ketone;
   (j) (4-Propylthiophenyl)-naphth-1-yl-ketone;
   (k) (4-Isopropylthiophenyl)-naphth-1-yl-ketone;
   (l) (4-Dimethylaminoethylthio-phenyl)naphth-1-yl-ketone;
   (m) (4-Diethylaminoethylthio-phenyl)-naphth-1-yl-ketone;
   (n) (4-Pyrrolidinoethylthio-phenyl)-naphth-1-yl-ketone; or
   (o) (4-Piperidinoethylthio-phenyl)-naphth-1-yl-ketone.

10. The pharmaceutical composition as defined by claim 8, formulated as gelatin capsules or compressed into tablets or pills, or formulated in the form of lozenges, inclusion complexes with cyclodextrin derivatives, injectable depo formulations, aerosols, granules, powders, oral liquids, mucosal adhesive formulations, gel formulations, troches, elixirs, suspensions, syrups, wafers, liposomal delivery systems, implants, suppository, pessary, microemulsions, nanoemulsion, microparticles, nanoparticles, controlled release delivery systems, transdermal delivery systems, targeted delivery systems, conjugates with monoclonal antibodies or with other suitable carrier moieties.

11. The pharmaceutical composition as defined by claim 8, comprising a pharmaceutically acceptable salt selected from the group consisting of formate, acetate, phenyl acetate, trifluoroacetate, acrylate, ascorbate, benzoate, chlorobenzoates, bromobenzoates, iodobenzoates, nitrobenzoates, hydroxybenzoates, alkylbenzoates, alkyloxybenzoates, alkoxycarbonylbenzoates, naphthalene-2 benzoate, butyrates, phenylbutyrates, hydroxybutyrates, caprate, caprylate, cinnamate, mandelate, mesylate, citrate, tartarate, fumarate, heptanoate, hippurate, lactate, malate, maleate, malonate, nicotinate, isonicotinate, oxalate, phthalate, terephthalate, phosphate, monohydrogen phosphate, dihydrogen phosphate, metaphosphate, pyrophosphate, propiolate, propionate, phenylpropionate, salicylate, sebacate, succinate, suberate, sulfate, bisulfate, pyrosulfate, sulfite, bisulfate, sulfonate, benzene sulfonate, bromobenzene sulfonates, chlorobenzene sulfonates, ethane sulfonates, methane sulfonates, naphthalene sulfonates, toluene sulfonates, and compounds thereof.

12. The pharmaceutical composition as defined by claim 8, comprising a pharmaceutically acceptable diluent selected from the group consisting of a lactose, mannitol, sorbitol, microcrystalline cellulose, sucrose, sodium citrate, dicalcium phosphate, or any other ingredient of similar nature alone or in a suitable combination thereof; binder selected from the group consisting of gum tragacanth, gum acacia, methyl cellulose, gelatin, polyvinyl pyrrolidone, starch or any other ingredient of similar nature alone or in a suitable combination thereof; excipient selected from the group consisting of agar-agar, calcium carbonate, sodium carbonate, silicates, alginic acid, corn starch, potato tapioca starch, primogel or any other ingredient of similar nature alone or in a suitable combination thereof; lubricant selected from the group consisting of a magnesium stearate, calcium stearate or steorotes, talc, solid polyethylene glycols, sodium lauryl sulfate or any other ingredient of similar nature alone or in a suitable combination thereof; glidant selected from the group consisting of colloidal silicon dioxide or any other ingredient of similar nature alone or in a suitable combination thereof; a sweetening agent selected from the group consisting of sucrose, saccharin or any other ingredient of similar nature alone or in a suitable combination thereof; a flavoring agent selected from the group consisting of peppermint, methyl salicylate, orange flavor, vanilla flavor, or any other pharmaceutically acceptable flavor alone or in a suitable combination thereof; wetting agent selected from the group consisting of acetyl alcohol, glyceryl monostearate or any other pharmaceutically acceptable flavor alone or in a suitable combination thereof; absorbent selected from the group consisting of kaolin, bentonite clay or any other pharmaceutically acceptable flavor alone or in a suitable combination thereof retarding agent selected from the group consisting of wax, paraffin or any other pharmaceutically acceptable flavor alone or in a suitable combination thereof.

13. The pharmaceutical composition as defined by claim 8, comprising from 0.1 mg to 1000 mg of said compound of formula 1.

14. The pharmaceutical composition as defined by claim 8, comprising from 0.5 mg to 500 mg of said compound of formula 1.

15. The pharmaceutical composition as defined by claim 8, comprising from 1 mg to 100 mg of said compound of formula 1.

* * * * *